(12) United States Patent
Barrish et al.

(10) Patent No.: US 6,239,133 B1
(45) Date of Patent: May 29, 2001

(54) IMIDAZOQUINOXALINE PROTEIN TYROSINE KINASE INHIBITORS

(75) Inventors: Joel C. Barrish, Richboro; Steven H. Spergel, Warrington, both of PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/566,002

(22) Filed: May 5, 2000

Related U.S. Application Data

(63) Continuation of application No. 09/094,297, filed on Jun. 15, 1998.
(60) Provisional application No. 60/056,797, filed on Aug. 25, 1997.

(51) Int. Cl.⁷ .......................... C07D 471/14; A61K 31/50
(52) U.S. Cl. ............................................ 514/250; 544/346
(58) Field of Search ............................... 544/346; 514/250

(56) References Cited

U.S. PATENT DOCUMENTS

| | | | |
|---|---|---|---|
| 4,160,097 | 7/1979 | Warner et al. | 548/346 |
| 4,172,947 | 10/1979 | Warner et al. | 548/346 |
| 4,191,766 | 3/1980 | Warner et al. | 424/250 |
| 4,191,767 | 3/1980 | Warner et al. | 424/250 |
| 4,197,403 | 4/1980 | Warner et al. | 544/346 |
| 4,198,508 | 4/1980 | Warner et al. | 544/346 |
| 4,200,750 | 4/1980 | Warner et al. | 544/346 |
| 4,225,724 | 9/1980 | Warner et al. | 548/346 |
| 4,229,452 | 10/1980 | Warner et al. | 424/250 |
| 4,236,015 | 11/1980 | Warner et al. | 548/346 |
| 4,317,682 | 3/1982 | Katsura et al. | 106/288 |
| 4,440,929 | 4/1984 | Lee et al. | 544/346 |
| 5,034,530 | 7/1991 | Hansen et al. | 544/346 |
| 5,276,028 | 1/1994 | Hansen | 514/228.5 |

FOREIGN PATENT DOCUMENTS

| | | |
|---|---|---|
| 728481 | 8/1996 | (EP) . |
| 92/00298 * | 1/1992 | (WO) . |
| WO97/19079 | 5/1997 | (WO) . |
| 99/10341 * | 3/1999 | (WO) . |

OTHER PUBLICATIONS

Davey et al., J. Med. Chem. 34: 2671–2677 (1991).
Wong et al., Eur. J. Pharmacol. 289: 335–342 (1995).
Rubino et al., Org. Mass Spectrom, 26: 636–644 (1991).
Regueiro et al., Chapter 6: Functional T cell defects, Human T lymphocyte activation deficiencies, R.G Landes Company, pp. 82–99 (1994).
Bolen, J.B., et al., FASEB Journal, vol. 6, pp. 3403–3409 (1992).
Chan, A.C., et al., EMBO Journal, vol. 14, pp. 24–99–2508 (1995).
Ihle, J.N., Seminars in Immunology, vol. 7, pp. 247–254 (1995).
Iwashima, M. et al., Science, vol. 263, pp. 1136–1139 (1994).
Schieven, G.L. et al., Journal of Biological Chemistry, vol. 269, No. 32, pp. 20718–20726 (1994).
Ulrich, A. et al., Cell, vol. 61, pp. 203–212, (1990).
Weiss, A., et al., Cell, vol. 76, pp. 263–274 (1994).
Cooper, J.A. et al., Journal of Biological Chemistry, vol. 259, No. 12, pp. 7835–7841 (1984).
CAS Printout for US 5,034,530, Jul. 1991.*

* cited by examiner

Primary Examiner—Bruck Kifle
Assistant Examiner—Hong Liu
(74) Attorney, Agent, or Firm—Ronald S. Hermenau

(57) ABSTRACT

Novel imidazoquinoxalines and salts thereof, pharmaceutical compositions containing such compounds, and methods of using such compounds in the treatment of protein tyrosine kinase-associated disorders such as immunologic disorders.

18 Claims, No Drawings

IMIDAZOQUINOXALINE PROTEIN TYROSINE KINASE INHIBITORS

This application is a continuation in part of U.S. application Ser. No. 09/094,797 filed Jun. 15, 1998, which claims priority from provisional U.S. application Ser. No. 60/056,797, filed Aug. 25, 1997, the entirety of which applications is each incorporated herein by reference.

FIELD OF THE INVENTION

The present invention relates to imidazoquinoxalines and salts thereof, to methods of using such compounds in treating protein tyrosine kinase-associated disorders such as immunologic disorders, and to pharmaceutical compositions containing such compounds.

BACKGROUND OF THE INVENTION

Protein tyrosine kinases (PTKs) are enzymes which, in conjuction with ATP as a substrate, phosphorylate tyrosine residues in peptides and proteins. These enzymes are key elements in the regulation of cell signaling including cell proliferation and cell differentiation. PTKs comprise, inter alia, receptor tyrosine kinases (RPTKs), including members of the epidermal growth factor kinase family (e.g., HER1 and HER2), platelet derived growth factor (PDGF), and kinases that play a role in angiogenesis (Tie-2 and KDR); and, in addition, non-receptor tyrosine kinases, including members of the Syk, JAK and Src (e.g. src, fyn, lyn, Lck and blk) families (see Bolen, J. B., Rowley, R. B., Spana, C., and Tsygankov, A. Y., "The src family of tyrosine protein kinases in hemopoietic signal transduction", *FASEB J.*, 6, 3403–3409 (1992); Ullrich, A. and Schlessinger, J., "Signal transduction by receptors with tyrosine kinase activity", *Cell*, 61, 203–212 (1990); and Ihle, J. N., "The Janus protein tyrosine kinases in hematopoetic cytokine signaling", *Sem. Immunol.*, 7, 247–254 (1995)).

Enhanced activity of PTKs has been implicated in a variety of malignant and nonmalignant proliferative diseases. In addition, PTKs play a central role in the regulation of cells of the immune system. PTK inhibitors can thus impact a wide variety of oncologic and immunologic disorders. Such disorders may be ameliorated by selective inhibition of a certain receptor or non-receptor PTK, such as Lck, or due to the homology among PTK classes, by inhibition of more than one PTK by an inhibitor.

A PTK of particular interest is Lck which is found in T cells where it is involved in phosphorylating key protein substrates. It is required for productive antigen receptor signaling and cell activation. In the absence of Lck activity, the T cell receptor (TCR) zeta chain is not phosphorylated, the kinase ZAP-70 is not activated, and $Ca^{2+}$ mobilization essential for T cell activation does not occur (see Weiss, A. and Littman, D. R. "Signal transduction by lymphocyte antigen receptors", *Cell*, 76, 263–274 (1994); Iwashima, M., Irving, B. A., van Oers, N. S. C., Chan, A. C., and Weiss, A., "Sequential interactions of the TCR with two distinct cytoplasmic tyrosine kinases", *Science*, 263, 1136–1139 (1994); and Chan, A. C., Dalton, M., Johnson, R., Kong, G., Wang, T., Thoma, R., and Kurosaki, T., "Activation of ZAP-70 kinase activity by phosphorylation of tyrosine 493 is required for lymphocyte antigen receptor function", *EMBO J.*, 14, 2499–2508 (1995)). Inhibitors of Lck are thus useful in the treatment of T-cell mediated disorders such as chronic diseases with an important T cell component, for example rheumatoid arthritis, multiple sclerosis and lupus, as well as acute diseases where T cells are known to play an essential role, for example acute transplant rejection and delayed-type hypersensitivity (DTH) reactions.

SUMMARY OF THE INVENTION

The present invention provides imidazoquinoxaline compounds of the following formula I and salts thereof, for use as protein tyrosine kinase inhibitors:

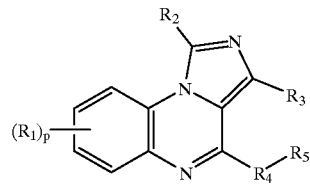

(I)

where
p is 0, 1, 2, 3 or 4;
each $R_1$, and $R_2$ and $R_3$, are independently selected from:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more (preferably, one or two) groups $Z_3$;
(2) —OH or —$OR_6$;
(3) —SH or —$SR_6$;
(4) —C(O)$_q$H, —C(O)$_q R_6$, or —O—C(O)$_q R_6$, where q is 1 or 2;
(5) —$SO_3$H or —S(O)$_q R_6$;
(6) halo;
(7) cyano;
(8) nitro;
(9) —$Z_4$—$NR_7 R_8$;
(10) —$Z_4$—N($R_9$)—$Z_5$—$NR_{10} R_{11}$;
(11) —$Z_4$—N($R_{12}$)—$Z_5$—$R_6$;
(12) —$SiR_{13} R_{14} R_{15}$;
(13) —P(O)(O$R_6$)$_2$;
(14) —CH=N—O$R_6$;
(15) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
(16) any two groups $R_1$ may, together with the carbons to which they are attached, form a heterocyclo group, which group is unsubstituted or substituted with $Z_1$, $Z_2$ and $Z_3$;

$R_4$ is oxygen, sulfur, or a single bond;
$R_5$ is alkyl, alkenyl, aryl, heterocyclo (preferably, heteroaryl), each of which is unsubstituted or substituted with $Z_1$, $Z_2$ and one or more (preferably, one or two) groups $Z_3$;
$R_7$, $R_8$, $R_9$, $R_{10}$, $R_{11}$ and $R_{12}$:
(1) are each independently hydrogen or $R_6$;
(2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$, $R_{14}$ and $R_{15}$ are each independently:
(1) alkyl; or
(2) phenyl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) $C(O)_qH$, —$C(O)_qZ_6$, or —O—$C(O)_qZ_6$;
(5) —$SO_3H$ or —$S(O)_qZ_6$;
(6) halo;
(7) cyano;
(8) nitro;
(9) —$Z_4$—$NZ_7Z_8$;
(10) —$Z_4$—$N(Z_9)$—$Z_5$—$NZ_7Z_8$;
(11) —$Z_4$—$N(Z_{10})$—$Z_5$—$Z_6$;
(12) —$Z_4$—$N(Z_{10})$—$Z_5$—H;
(13) oxo;
(14) —O—$C(O)$—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—$(CH_2)_q$—O—;

$Z_4$ and $Z_5$ are each independently:
(1) a single bond;
(2) —$Z_{11}$—$S(O)_q$—$Z_{12}$—;
(3) —$Z_{11}$—$C(O)$—$Z_{12}$—;
(4) —$Z_{11}$—$C(S)$—$Z_{12}$—;
(5) —$Z_{11}$—O—$Z_{12}$—;
(6) —$Z_{11}$—S—$Z_{12}$—;
(7) —$Z_{11}$—O—$C(O)$—$Z_{12}$—; or
(8) —$Z_{11}$—$C(O)$—O—$Z_{12}$—;

$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_9$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and $Z_{11}$ and $Z_{12}$ are each independently:
(1) a single bond;
(2) alkylene;
(3) alkenylene; or
(4) alkynylene.

Compounds of the formula I and salts thereof, excluding the compounds 4-methoxyimidazo[1,5-a]quinoxaline-3-carboxylic acid methyl ester and 4-(2-ethoxyethoxy)imidazo[1,5-a]quinoxaline-3-carboxylic acid ethyl ester, are novel.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a straight chain bridge of 1 to 5 carbon atoms connected by single bonds (e.g., —$(CH_2)_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —$CH_2$—CH=CH—, —$CH_2$—CH=CH—$CH_2$—, —$C(CH_3)_2$CH=CH— and —CH($C_2H_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —$CH_2$—C≡C—, —CH($CH_3$)—C≡C— and —C≡C—CH($C_2H_5$)$CH_2$—.

The terms "ar" or "aryl" refer to phenyl, naphthyl and biphenyl.

The terms "cycloalkyl" and "cycloalkenyl" refer to cyclic hydrocarbon groups of 3 to 8 carbon atoms.

The terms "halogen" and "halo" refer to fluorine, chlorine, bromine and iodine.

The term "unsaturated ring" includes partially unsaturated and aromatic rings.

The terms "heterocycle", "heterocyclic" or "heterocyclo" refer to fully saturated or unsaturated, including aromatic ("heteroaryl") or nonaromatic cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydroazepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), dihydrobenzodioxinyl (such as 2,3-dihydro-1,4-benzodioxinyl), benzodioxolyl (such as 1,3-benzodioxolyl), tetrahydroquinolinyl and the like.

Exemplary tricyclic heterocyclic groups include carbazolyl, benzidolyl, phenanthrolinyl, acridinyl, phenanthridinyl, xanthenyl and the like.

Where q is 1 or 2, "—$C(O)_qH$" denotes —C(O)—H or —C(O)—OH; "—$C(O)_qR_6$" or "—$C(O)_qZ_6$" denote, respectively, —C(O)—$R_6$ or —C(O)—$OR_6$, or —C(O)—$Z_6$ or —C(O)—$OZ_6$; "—O—$C(O)_qR_6$" or "—O—$C(O)_qZ_6$" denote, respectively, —O—C(O)—$R_6$ or —O—C(O)—$OR_6$, or —O—C(O)—$Z_6$ or —O—C(O)—$OZ_6$; and "—S$(O)_qR_6$" or "—S$(O)_qZ_6$" denote, respectively, —SO—$R_6$ or —$SO_2$—$R_6$, or —SO—$Z_6$ or —$SO_2$—$Z_6$.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates. Any tautomers which may exist are also contemplated herein as part of the present invention.

All stereoisomers of the present compounds, such as those which may exist due to asymmetric carbons on the R substituents of the compound of the formula I, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Throughout the specification, groups and substituents thereof are chosen to provide stable moieties and compounds.

Preferred Compounds

Compounds of the formula I, and salts thereof, wherein one or more, and especially all, of p, $R_1$, $R_2$, $R_3$, $R_4$, and $R_5$ are selected from the following definitions, are preferred compounds of the present invention:

p is 0, 1 or 2;

each $R_1$ is independently selected from hydrogen, alkyl, alkoxy, nitro, aryl, halo, heterocyclo, —$Z_4$—$NR_7R_8$ or —$Z_4$—$N(R_{12})$—$Z_5$—$R_6$;

$R_2$ is selected from hydrogen or alkyl;

$R_3$ is selected from hydrogen or alkyl;

$R_4$ is selected from oxygen, sulfur, or a single bond; and $R_5$ is selected from optionally substituted aryl.

Preferred compounds also include those compounds where $R_3$ is other than hydrogen, cyano, tetrazolo, carboxaldehyde, hydroxyalkyl carboxylic acid, or ester or amide derivatives thereof when 1) $R_2$ is hydrogen, alky, aryl, halo, amino, alkylamino, arylamino, hydroxyamino, hydroxy, alkoxy, mercapto or alkylthio; and 2) $R_4$ and $R_5$ together form alkyl, aryl, alkoxy or alkylthio.

Methods of Preparation

The compounds of the formula I may be prepared by methods such as those illustrated in the following Schemes I to IV. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art.

The methods described herein may be carried out with starting materials and/or reagents in solution or alternatively, where appropriate, with one or more starting materials or reagents bound to a solid support (see (1) Thompson, L. A., Ellman, J. A., *Chemical Reviews*, 96, 555–600 (1996); (2) Terrett, N. K., Gardner, M., Gordon, D. W., Kobylecki, R. J., Steele, J., *Tetrahedron*, 51, 8135–8173 (1995); (3) Gallop, M. A., Barrett, R. W., Dower, W. J., Fodor, S. P. A., Gordon, E. M., *Journal of Medicinal Chemistry*, 37, 1233–1251 (1994); (4) Gordon, E. M., Barrett, R. W., Dower, W. J., Fodor, S. P. A., Gallop, M. A., *Journal of Medicinal Chemistry*, 37, 1385–1401 (1994); (5) Balkenhohl, F., von dem Bussche-Hünnefeld, Lansky, A., Zechel, C., *Angewandte Chemie International Edition in English*, 35, 2288–2337 (1996); (6) Balkenhohl, F., von dem Bussche-Hünnefeld, Lansky, A., Zechel, C., *Angewandte Chemie*, 108, 2436–2487 (1996); and (7) Sofia, M. J., *Drugs Discovery Today*, 1, 27–34 (1996)).

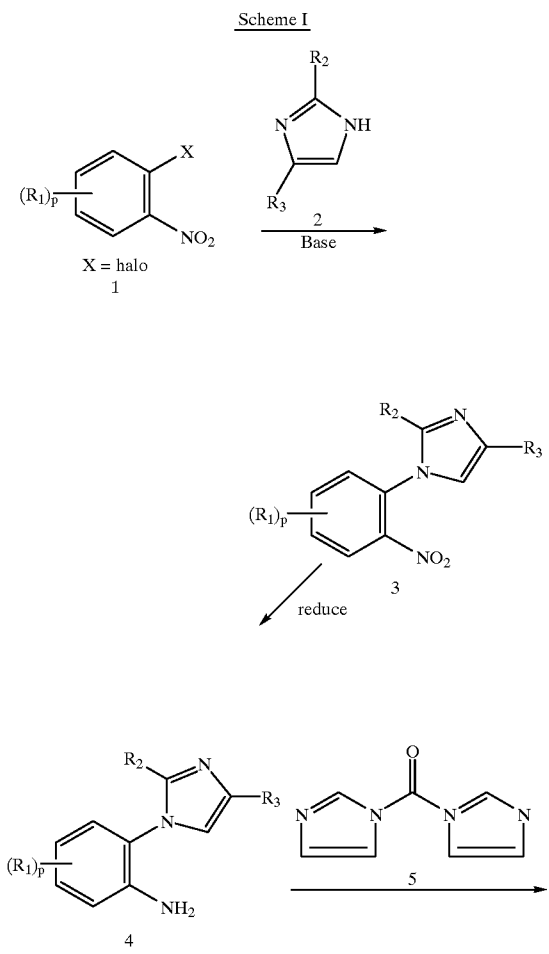

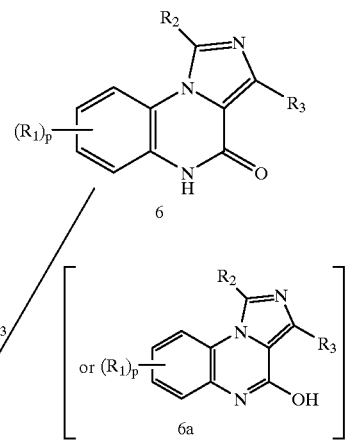

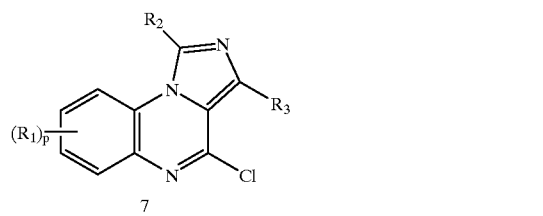

As shown in Scheme I, an appropriately substituted 2-nitro halobenzene 1 can be reacted with a substituted imidazole 2 in the presence of a base such as sodium, potassium, or cessium carbonate, or an amine base such as triethyl amine, diisopropylethyl amine, 1,8-diazabicyclo[5.4.0]undec-7-ene ("DBU"), or the like, in an appropriate solvent to give the imidazole derivative 3 (Davey, et al., *J. Med. Chem.*, 34, 2671 (1991)). The reaction may also be carried out in the presence of a copper I salt such as cuprous chloride, cuprous bromide, or cuprous iodide (Sitkina, et al., *Khim Geterotskil Soed* in 143 (1966); Grimmett, et al., *Aust. J. Chem.*, 32, 2203 (1979); Sugaya, et al., *Synthesis*, 73 (1994)). Preferred X groups in 1 are F and Cl in the absence of a copper I salt and Br and I in the presence of a copper I salt.

The nitro group of 3 may then be reduced to provide the corresponding amine 4 by methods such as those known in the art (e.g., Hudlicky, "Reductions in Organic Chemistry", Wiley (1984)), for example, by catalytic hydrogenation, or by use of $SnCl_2$, $FeCl_3$, sodium dithionite, or the like.

The aminoimidazole derivative 4 may be reacted with carbonyldiimidazole 5, or alternatively phosgene or phosgene equivalents, to give the quinoxolinone 6 (Davey, et al., *J. Med. Chem.*, 34, 2671 (1991)). Quinoxolinone 6 may also exist as its tautomer 6a.

When $R_2$ is hydrogen a mixture of regioisomers is possible at the imidazole ring, and the desired 1,6-isomer is preferably separated from the 1,2-isomer by methods such as fractional crystallization, or chromatography on silica gel or C-18. It is preferred to obtain a compound of the formula I substantially free of its corresponding 1,2-regioisomer. Quinoxolinone 6 may be converted into its chloroimidate 7 in the presence of phosphorylchloride, or analogous reagents such as $SOCl_2$, $PCl_5$, $PPh_3/CCl_4$, or the like, and 7 reacted with the appropriate alcohol or thiol 8 in the presence of a base such as sodium or potassium hydride, or the like (see *J. Med. Chem.*, 36, 2335 (1993); and *Collect. Czech. Chem. Commun.*, 55, 2493 (1990)), or the appropriate organometallic reagent 9 where M is an organometallic group such as a Grignard, organolithium, organotin, or boronic acid derivative, or the like (see *Tetrahedron Lett.*, 32, 2273 (1991); and *J. Chem. Soc. C*, 2376 (1969)) to give compound I.

Scheme II

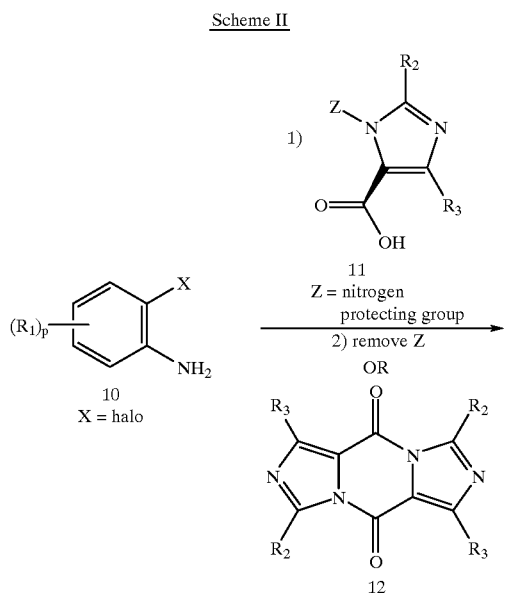

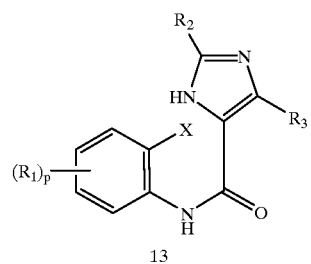

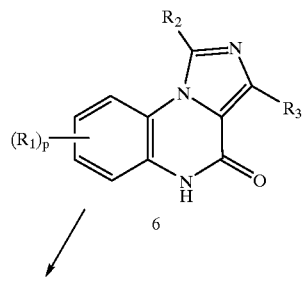

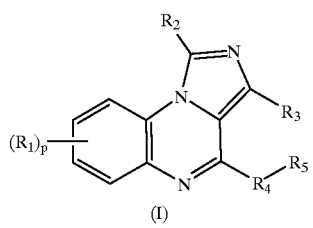

As shown in Scheme II, an appropriately substituted amino alobenzene 10 may be converted to the corresponding amide 13 by either of two methods: 1) direct coupling with the N-protected imidazole carboxylic acid 11 using peptide coupling procedures such as standard methods known in the art (see, for example, Bodanszky, "Principles of peptide synthesis", Springer-Verlag (1984); Bodanszky and Bodansky, "The Practice of Peptide Chemistry", Springer-Verlag (1984)), followed by removal of the Z protecting group (see, for example, Greene, "Protective Groups in Organic Synthesis", Wiley (1991)); or 2) reaction of 10 with the dimer 12, the latter prepared by methods such as those known in the art (Kasina and Nematollahi, *Synthesis*, 162 (1975); Godefrol, et al., *J. Org. Chem.*, 29, 3707 (1964)). Exemplary nitrogen protecting groups include carbobenzyloxy or t-butoxycarbonyl. The dimer 12 may also be prepared by coupling the imidazole carboxylic acid:

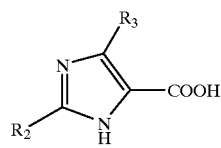

employing thionyl chloride or oxalyl chloride, preferably in the presence of dimethylformamide and heat.

Amide 13 may then be converted to the quinoxolinone 6 by treatment with a base such as sodium, potassium, or cessium carbonate or an amine base such as triethylamine, diisopropylamine, DBU, or the like; or in the presence or absence of a copper I salt such as cuprous chloride, cuprous bromide, or cuprous iodide. Preferred X groups in 13 are F and Cl in the absence of a copper (I) salt and Br and I in the presence of a copper (I) salt. Conversion of 6 to compound I may then be carried out as described in Scheme I.

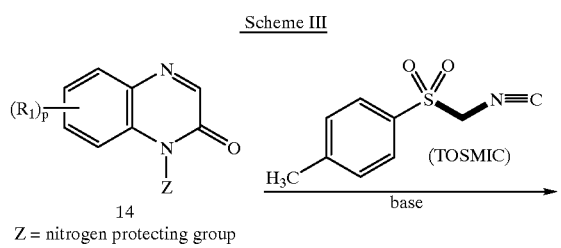

As shown in Scheme III, the protected quinoxolone 14 may be reacted with tosylmethylisocyanide ("TOSMIC") in the presence of a base such as sodium hydride, n-butyl lithium, lithium, sodium, potassium, or cessium carbonate, or the like, to give the imidazoquinoxolone 15 (Silvestri, et al., *J. Heterocyclic Chem.*, 31, 1033 (1994); Massa, et al., *J. Heterocyclic Chem.*, 30, 749 (1993)). After removal of the nitrogen protecting group Z, conversion of 15 to compound I ($R_2$, $R_3$=H) can be carried out by methodology described in Scheme I.

The starting materials for this Scheme are commercially available or may be readily prepared as described, for example, in 1) Japanese Patent JPO 5140120; 2) Epperson, et al., *Bioorg. Med. Chem. Lett.*, 3, 2801 (1993); 3) Bekerman, et al., *J. Heterocycl. Chem.*, 29, 129 (1992); 4) Kazimierczuk and Pfleiderer, *Liebigs Ann. Chem.*, 754 (1982); 5) a) Kalyanam and Manjunatha, *Indian J. Chem.*, Sect. B, 31, 415 (1992) and b) Wear and Hamilton, *J. Am. Chem. Soc.*, 72, 2893 (1950); and 6) Sakaata, et al., *Heterocycles*, 23, 143 (1983).

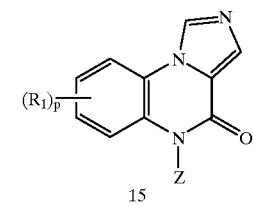

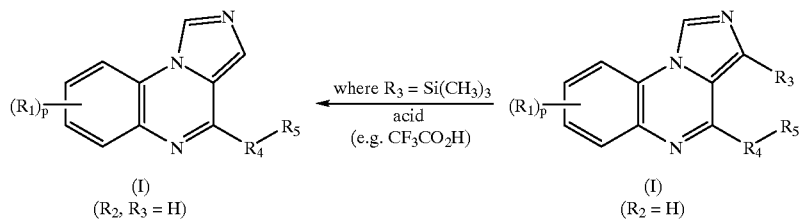

As shown in Scheme IV, a chloro- or dichloroquinoxoline 16 may be reacted with 1 equivalent of 8 or 9 by methods described in Scheme I. Where Y=Cl in 17, treatment with an isocyanide 18 and base as described in Scheme III gives Compound I ($R_2$=H) (Jacobsen, et al., *J. Med. Chem.*, 39, 3820 (1996)). R, is selected such that the anion of 18 can readily form. When $R_3$ is a trimethylsilyl (TMS) group, it can subsequently be removed by protodesilylation with an acid such as trifluoracetic acid (Funk & Vollhardt, *J. Am. Chem. Soc.*, 99, 5483 (1977)) to give compound I ($R_2$, $R_3$=H). Alternatively, the above order of addition may be reversed whereby isocyanide 18 is first added to 16 (Y=Cl) followed by 8 or 9.

Where Y=H in 17, TOSMIC and base may be added as described in Scheme III to give compound I ($R_2$, $R_3$=H).

The starting materials for this Scheme are commercially available or may be prepared, for example, as described in Curd et al., *J. Chem. Soc.*, 1271 (1949).

Utility

The compounds of the present invention inhibit protein tyrosine kinases, especially Src-family kinases such as Lck, Fyn, Lyn, Src, Yes, Hck, Fgr and Blk, and are thus useful in the treatment, including prevention and therapy, of protein tyrosine kinase-associated disorders such as immunologic disorders. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a particularly preferred embodiment of the present invention. Compounds which selectively block T cell activation and proliferation are preferred. Compounds of the present invention which block the activation of endothelial cell PTK by oxidative stress, thereby limiting surface expression of adhesion molecules that induce neutrophil binding, and which inhibit PTK necessary for neutrophil activation are useful, for example, in the treatment of ischemia and reperfusion injury.

The present invention thus provides methods for the treatment of protein tyrosine kinase-associated disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compounds of the present invention in treating protein tyrosine kinase-associated disorders is exemplified by, but is not limited to, treating a range of disorders such as: transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracierma; mycosis fingoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides a method for treating the aforementioned disorders such as atopic dermatitis by administration of any compound capable of inhibiting protein tyrosine kinase.

Src-family kinases other than Lck, such as Hck and Fgr, are important in the Fc gamma receptor induced respiratory burst of neutrophils as well as the Fc gamma receptor responses of monocytes and macrophages. The compounds of the present invention inhibit the Fc gamma induced respiratory burst response in neutrophils, and also inhibit the Fc gamma dependent production of TNF alpha in the monocyte cell line THP-1 that does not express Lck. The ability to inhibit Fc gamma receptor dependent neutrophil, monocyte and macrophage responses results in additional anti-inflammatory activity for the present compounds beyond their effects on T cells. This activity is especially of value, for example, in the treatment of inflammatory diseases such as arthritis or inflammatory bowel disease. In particular, the present compounds are of value for the treatment of autoimmune glomerulonephritis and other instances of glomerulonephritis induced by deposition of immune complexes in the kidney that trigger Fe gamma receptor responses leading to kidney damage.

In addition, Src family kinases other than Lck, such as Lyn and Src, are important in the Fc epsilon receptor induced degranulation of mast cells and basophils that plays an important role in asthma, allergic rhinitis, and other allergic disease. Fc epsilon receptors are stimulated by IgE-antigen complexes. The compounds of the present invention inhibit the Fc epsilon induced degranulation responses, including in the basophil cell line RBL that does not express Lck. The ability to inhibit Fc epsilon receptor dependent mast cell and basophil responses results in additional anti-inflammatory activity for the present compounds beyond their effect on T cells. In particular, the present compounds are of value for the treatment of asthma, allergic rhinitis, and other instances of allergic disease.

The combined activity of the present compounds towards monocytes, macrophages, T cells, etc. may be of value in the treatment of any of the aforementioned disorders.

In a particular embodiment, the compounds of the present invention are useful for the treatment of the aforementioned exemplary disorders irrespective of their etiology, for example, for the treatment of transplant rejection, rheumatoid arthritis, multiple sclerosis, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

The present invention also provides pharmaceutical compositions comprising at least one of the compounds of the formula I capable of treating a protein tyrosine kinase-associated disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to protein tyrosine kinase-associated disorders.

The compounds of the present invention may be employed alone or in combination with each other and/or other suitable therapeutic agents useful in the treatment of protein tyrosine kinase-associated disorders such as PTK inhibitors other than those of the present invention, antiinflammatories, antiproliferatives, chemotherapeutic agents, and immunosuppressants.

Exemplary such other therapeutic agents include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, steroids such as prednisone or dexamethasone, gold compounds, antiproliferative agents such as methotrexate, FK506 (tacrolimus, Prograf), mycophenolate mofetil, cytotoxic drugs such as azathiprine and cyclophosphamide, TNF-$\alpha$ inhibitors such as tenidap, anti-TNF antibodies or soluble TNF receptor, and rapamycin (sirolimus or Rapamune) or derivatives thereof, and the PTK inhibitors disclosed in the following U.S. Patent Applications, incorporated herein by reference in their entirety: Ser. No. 60/069,159, filed Dec. 9, 1997 Ser. No. 09/097,338, filed concurrently herewith by Joel C. Barrish et al., "Imidazoquinoxaline Protein Tyrosine Kinase Inhibitors" Ser. No. 60/065,042, filed Nov. 10, 1997, and Ser. No. 60/076,789, filed Mar. 4, 1998. See the following documents and references cited therein: Hollenbaugh, D., Douthwright, J., McDonald, V., and Aruffo, A., "Cleavable CD40Ig fusion proteins and the binding to sgp39", *J. Immunol. Methods* (Netherlands), 188(1), p. 1–7 (Dec. 15, 1995); Hollenbaugh, D., Grosmaire, L. S., Kullas, C. D., Chalupny, N. J., Braesch-Andersen, S., Noelle, R. J., Stamenkovic, I., Ledbetter, J. A., and Aruffo, A., "The human T cell antigen gp39, a member of the TNF gene family, is a ligand for the CD40 receptor: expression of a soluble form of gp39 with B cell co-stimulatory activity", *EMBO J* (England), 11(12), p 4313–4321 (December 1992); and Moreland, L. W. et al., "Treatment of rheumatoid arthritis with a recombinant human tumor necrosis factor receptor (p75)-Fc fusion protein, *New England J. of Medicine*, 337(3), p. 141–147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The following assays can be employed in ascertaining the degree of activity of a compound ("test compound") as a PTK inhibitor. Compounds described in the following Examples have been tested in one or more of these assays, and have shown activity.

Lck Enzyme Assay

Recombinant Lck expressed as a His-tagged fusion protein in insect cells using a baculovirus expression system and purified by nickel affinity chromatography is incubated in kinase buffer (20 mM MOPS, pH7, 10 mM $MgCl_2$) in the presence of the test compound. The reaction is initiated by the addition of substrates to the final concentration of 1 $\mu$M ATP, 3.3 $\mu$Ci/ml [33P] g-ATP, and 0.1 mg/ml acid denatured enolase (prepared as described in Cooper, J. A., Esch, F. S., Taylor, S. S., and Hunter, T., "Phosphorylation sites in enolase and lactate dehydrogenase utilized by tyrosine protein kinases in vivo and in vitro", *J. Biol. Chem.*, 259, 7835–7841 (1984)). The reaction is stopped after 10 minutes by the addition of 10% trichloroacetic acid, 100 mM sodium pyrophosphate followed by 2 mg/ml bovine serum albumin. The labeled enolase protein substrate is precipitated at 4 degrees, harvested onto Packard Unifilter plates and counted in a Topcount scintillation counter to ascertain the Lck inhibitory activity of the test compound (activity inversely proportional to the amount of labeled enolase protein obtained). The exact concentration of reagents and the amount of label can be varied as needed.

This assay is advantageous as it employs an exogenous substrate (enolase) for more accurate enzyme kinetics, and can be conducted in a 96-well format that is readily automated. In addition, the His-tagged Lck offers much higher production yields and purity relative to GST-Lck fusion protein.

For the preparation of recombinant Lck: Human Lck was prepared as a His-tagged fusion protein using the Life Technologies (Gibco) baculovirus vector pFastBac Hta (commercially available) in insect cells. A cDNA encoding human Lck isolated by PCR (polymerase chain reaction) was inserted into the vector and the protein was expressed using the methods described by the manufacturer. For the production of Lck in insect cells using baculovirus, see Spana, C., O'Rourke, E. C., Bolen, J. B., and Fargnoli, J., "Analysis of the tyrosine kinase p56lck expressed as a glutathione S-transferase protein in *Spodoptera frugiperda* cells," *Protein expression and purification*, Vol. 4, p. 390–397 (1993).

Cell Assays (1) Cellular Tyrosine Phosphorylation

Jurkat T cells are incubated with the test compound and then stimulated by the addition of antibody to CD3 (monoclonal antibody G19-4). Cells are lysed after 4 minutes or at another desired time by the addition of a lysis buffer containing NP-40 detergent. Phosphorylation of proteins is detected by anti-phosphotyrosine immunoblotting. Detection of phosphorylation of specific proteins of interest such as ZAP-70 is detected by immunoprecipitation with anti—ZAP-70 antibody followed by anti-phosphotyrosine immunoblotting. Such procedures are described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and $H_2O_2$ induced T cell signal transduction", *J. Biol. Chem.*, 269, 20718–20726 (1994), and the references incorporated therein. The Lck inhibitors inhibit the tyrosine phosphorylation of cellular proteins induced by anti-CD3 antibodies.

For the preparation of G19-4, see Hansen, J. A., Martin, P. J., Beatty, P. G., Clark, E. A., and Ledbetter, J. A., "Human T lymphocyte cell surface molecules defined by the workshop monoclonal antibodies," in *Leukocyte Typing I*, A. Bernard, J. Boumsell, J. Dausett, C. Milstein, and S. Schlossman, eds. (New York: Springer Verlag), p. 195–212 (1984); and Ledbetter, J. A., June, C. H., Rabinovitch, P. S., Grossman, A., Tsu, T. T., and Imboden, J. B., "Signal transduction through CD4 receptors: stimulatory vs. inhibitory activity is regulated by CD4 proximity to the CD3/T cell receptor", *Eur. J. Immunol.*, 18, 525 (1988).

(2) Calcium Assay

Lck inhibitors block calcium mobilization in T cells stimulated with anti-CD3 antibodies. Cells are loaded with the calcium indicator dye indo-1, treated with anti-CD3 antibody such as the monoclonal antibody G19-4, and calcium mobilization is measured using flow cytometry by recording changes in the blue/violet indo-1 ratio as described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and $H_2O_2$ induced T cell signal transduction", *J. Biol. Chem.*, 269, 20718–20726 (1994), and the references incorporated therein.

(3) Proliferation assays

Lck inhibitors inhibit the proliferation of normal human peripheral blood T cells stimulated to grow with anti-CD3 plus anti-CD28 antibodies. A 96 well plate is coated with a monoclonal antibody to CD3 (such as G19-4), the antibody is allowed to bind, and then the plate is washed. The antibody bound to the plate serves to stimulate the cells. Normal human peripheral blood T cells are added to the wells along with test compound plus anti-CD28 antibody to provide co-stimulation. After a desired period of time (e.g., 3 days), the [3H]-thymidine is added to the cells, and after further incubation to allow incorporation of the label into newly synthesized DNA, the cells are harvested and counted in a scintillation counter to measure cell proliferation.

The following Examples illustrate embodiments of the present invention, and are not intended to limit the scope of the claims. Abbreviations employed in the Examples are defined below. Compounds of the Examples are identified by the example and step in which they are prepared (for example, "1A" denotes the title compound of step A of Example 1), or by the example only where the compound is the title compound of the example (for example, "2" denotes the title compound of Example 2).

Abbreviations aq.=aqueous
Boc=t-butoxycarbonyl
Bu=butyl
DMF=dimethylformamide
DMSO=dimethylsulfoxide
EtOAc=ethyl acetate
EtOH=ethanol
h=hours
hex=hexane
Me=methyl
MeOH=methanol
min.=minutes
MOPS=4-morpholine-propanesulfonic acid
MS=mass spectrometry
Ms=mesyl
n-Bu=n-butyl
Pd/C=palladium on carbon
Ph=phenyl
Ret Time=retention time
sat.=saturated
TFA=trifluoroacetic acid
THF=tetrahydrofuran
Ts=tosyl

EXAMPLE 1

Preparation of 4-Phenylimidazo[1,5-a]quinoxaline

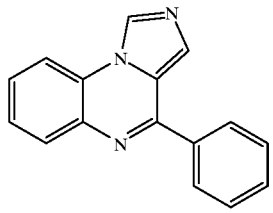

A. 2-Quinoxalinol

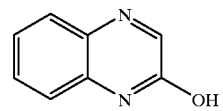

To a solution of 1,2-phenylene diamine (1.98 g, 18.34 mmol) in 25 mL of absolute EtOH was added a solution of ethyl glyoxylate in toluene (1.1 eq., 20.17 mmol, 19% w/w). The mixture was heated to reflux for 3 h. After cooling to room temperature, water (100 ml) was added. The precipitate was collected by filtration and washed with water, then dried under high vacuum to give 2.36 g (88%) of 1A as a beige-colored solid.

B. 1-[(4-Methoxyphenyl)methyl]-2(1H)-quinoxalinone

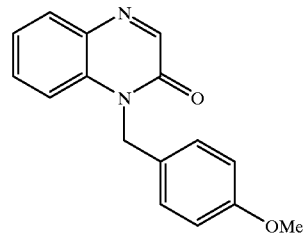

4.4 g of NaH (1.1 eq., 0.11 mol, 60% in mineral oil) was washed once with hexane and suspended in dry DMF (50 mL). To this suspension cooled at 0° C. was added 1A (14.6 g, 0.10 mol) in dry DMF (100 mL). The reaction mixture was stirred at ambient temperature for 30 min. After cooling to 0° C., a solution of 4-methoxy benzylchloride (14.9 mL, 0.11 mol) in 50 mL of dry DMF was added, followed by n-Bu$_4$NI (7.38 g, 0.2 eq., 20 mmol). The mixture was stirred at room temperature for 2 h, then was heated at 60° C. for 2 h. The reaction mixture was partitioned between sat. NH$_4$Cl solution and EtOAc and extracted with EtOAc. The combined extracts were washed with water and dried over anhydrous Na$_2$SO$_4$. Concentration in vacuo gave a crude product as an off-white solid. Trituration with ether overnight gave, after filtration, 14.2 g of 1B as an off-white solid (first crop). The mother liquid was concentrated and chromatographed (hexane-EtOAc: 3:1 to 1:1) on silica gel to give an additional 5.51 g of 1B as an off-white solid (74% combined yield).

C. 5-[(4-Methoxyphenyl)methyl]imidazo[1,5-a]quinoxalin-4(5H)-one

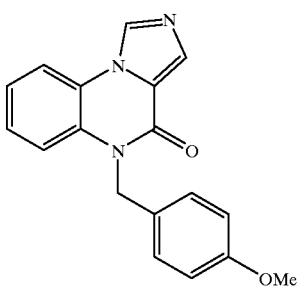

1.82 g of NaH (2.2 eq., 45.52 mmol, 60% in mineral oil) was washed once with hexane and suspended in dry THF (40 ml). To this suspension cooled at 0° C. was added a mixture of 1B (5.51 g, 20.7 mmol) and tosylmethyl isocyanide (4.44 g, 22.76 mmol) in dry THF (80 mL). The reaction mixture was stirred at 0° C. for 30 min, warmed to room temperature and stirred for an additional 1.0 h. The reaction mixture was poured onto a mixture of ice-water (1.5 L). The light beige-colored precipitate was collected by filtration and washed with water and dried under high vacuum. Trituration with MeOH and ether gave 5.72 g (94%) of 1C as a light beige solid.

D. Imidazo[1,5-a]quinoxalin-4(5H)-one

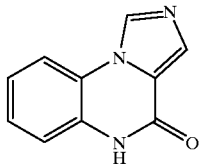

To a solution of 1C (7.69 g, 26.22 mmol) in 130 mL of trifluoroacetic acid was added 52 mL of anisole, followed by dropwise addition of 26 mL of trifluoromethane sulfonic acid. The mixture was stirred at room temperature overnight. Concentration in vacuo gave a residue which was added carefully via pipet to a mixture of cold saturated NaHCO$_3$. The resulting orange-yellow precipitate was collected by filtration and washed first with water, then ether to give 13.5 g of crude product after drying under high vacuum. This material was stirred in 1 L of MeOH overnight and the white precipitate was removed by filtration. The filtrate was concentrated in vacuo and the residue was again triturated with ether to give, after drying under high vacuum, 4.23 g (91%) of 1D as a light yellow solid.

1D was alternatively prepared as follows, employing as a starting material 1E(ii) prepared below:

To a solution of 1E(ii) (3.3 g, 16.1 mmol) in 30 mL dimethylacetamide was added K$_2$CO$_3$ (4.4 g, 32.16 mmol). The reaction mixture was heated to reflux for 18 h then the reaction was concentrated in vacuo and H$_2$O was added. The solid precipitate was filtered, rinsed with water, and dried under vacuum to give 2.49 g (84%) of 1D.

E. N-(2-Fluorophenyl)-1H-imidazole-4-carboxamide
  (i) Imidazolecarbonyl Dimer

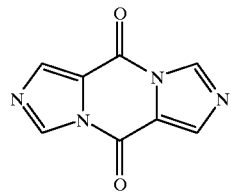

To 4-imidazolecarboxylic acid (5 g, 44.6 mmol) in toluene (100 mL) was added DMF (700 μL) followed by thionyl chloride (10 mL). The suspension was heated to reflux for 1.5 hours, then cooled to room temperature. The solid was filtered with toluene rinse, then supsended in 80 mL CHCl$_3$ followed by the addition of 12 mL triethylamine. The mixture was stirred for 2 hours at room temperature, then filtered with CHCl$_3$ rinse. The solid product was dried under vacuo to give 4.07 g (97%) of the title dimer 1E(i). 1E(i) can also be prepared by the method described in Kasina, S., Nematollahi, J., Synthesis, 162 (1975).

(ii) N-(2-Fluorophenyl)-1H-imidazole-4-carboxamide

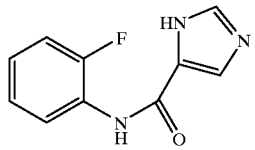

To a solution of 2-fluoroaniline (2.3 mL, 23.4 mmol) in 10 mL THF was added a solution of sodium bis(trimethylsilyl) amide (47 mL, 47 mmol) in THF. The mixture was heated to reflux for 0.5 h then cooled to room temperature. To the reaction mixture was added 1E(i) (2.2 g, 11.7 mmole) in 20 mL THF and heated to reflux for 2 h. The reaction mixture was cooled in ice, quenched with acetic acid and condensed in vacuo. Water was added to the residue and neutralized with NaHCO$_3$. The resulting solid precipitate was filtered and washed with water followed by hexane. Drying in vacuo gave 3.5 g (80%) of 1E(ii).

F. 4-Chloroimidazo[1,5-a]quinoxaline

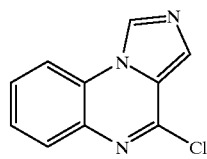

A mixture of 1D (2.16 g, 11.7 mmol) in 20 mL of phosphorus oxychloride was heated to reflux for 16 h. The reaction mixture was then concentrated in vacuo and azeotroped with toluene. The residue was then cooled in an ice bath and cold water was added. The aqueous layer was neutralized with NaHCO$_3$ and extracted with CH$_2$Cl$_2$. Concentration of the organic layer under reduced pressure gave 2.0 g (84%) of 1F.

G. 4-Phenylimidazo[1,5-a]quinoxaline

A mixture of 1F (51 mg; 0.25 mmol), phenylboronic acid (61 mg; 0.50 mmol), tetrakistriphenylphosphine palladium (5 mg), ethanol (0.8 mL), toluene (1 mL) and 2M sodium carbonate (0.7 mL) was stirred briskly at 80° C. for 1.5 hrs. After cooling to room temperature, the reaction mixture was partitioned between EtOAc and water. The organic layer was washed with brine, dried (MgSO$_4$) and concentrated. The residue was chromatographed on a 2.5×15 cm silica gel column, using EtOAc:Hex, 1:1 and EtOAc as the mobile phase. The pure fractions were concentrated to a residue that was subsequently dissolved in 2 mL of CH$_2$Cl$_2$. Hexane (8 mL) was added and the CH$_2$Cl$_2$ was removed in vacuo. The yellow crystals formed were filtered, rinsed with hexane and dried to afford 40 mg (66%) of the title product of this Example as a yellow crystalline solid. [mp 165–167° C.; HPLC: Retention time=7.79 minutes, (UV 217 nM); YMC S-3 ODS (C-18) 6.0×150 mm; 70% B:A-100% B (A=90% H$_2$O/10% MeOH+0.2% H$_3$PO$_4$; B=90% MeOH/10% H$_2$O+0.2% H$_3$PO$_4$) linear gradient over 25 minutes.]

EXAMPLE 2

Preparation of 4-(4-Methoxyphenyl)imidazo[1,5-a]quinoxaline

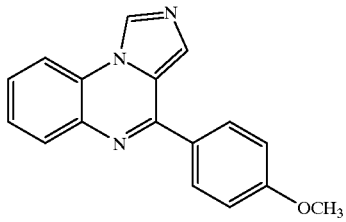

Analogous to the method described in Example 1 to give 54 mg (79%) of the title product as light yellow needles. [mp 187–188° C.; HPLC: Retention time=7.85 minutes, HPLC conditions as described in Example 1.]

EXAMPLE 3

Preparation of 4-(4-Fluorophenyl)imidazo[1,5-a]quinoxaline

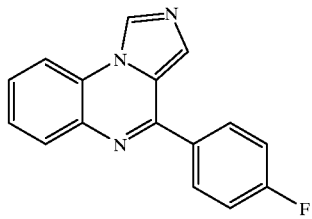

Analogous to the method described in Example 1 to give 19 mg (55%) of the title product as a yellow solid. [mp 214–215° C.; HPLC: Retention time=8.89 minutes, HPLC conditions as described in Example 1.]

EXAMPLE 4

Preparation of 4-(2,6-Dimethylphenyl)imidazo[1,5-a]quinoxaline

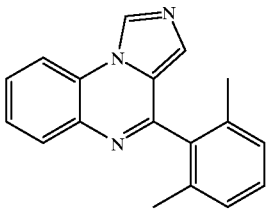

Analogous to the method described in Example 1 (the boronic acid employed was prepared as described in *Tetrahedron Lett.*, 33, 265 (1992)) to give 22 mg (55%) of the title product as a white powder. [mp 115–125° C.; HPLC: Retention time=8.24 minutes, HPLC conditions as described in Example 1.]

EXAMPLE 5

Preparation of 4-(2-Bromophenoxy)imidazo[1,5-a]quinoxaline

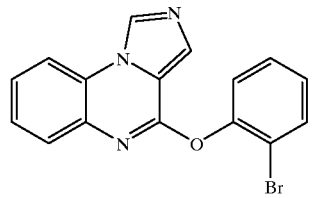

A mixture of 1F (40 mg; 0.2 mmol), o-bromophenol (38 mg; 0.22 mmol) and potassium carbonate (70 mg; 0.5 mmol) in 0.5 mL of DMF was heated to 60° C. for 18 hr. After cooling, the reaction mixture was partitioned between EtOAc and water. The organic layer was washed with 1N NaOH, water, and brine. Drying (MgSO$_4$), concentration and crystallization from CH$_2$Cl$_2$/hexane afforded 57 mg (87%) of the title product as a tan crystalline solid. [mp 180–182° C.; HPLC: Retention time=12.04 minutes, HPLC conditions as described in Example 1.]

EXAMPLE 6

Preparation of 4-[(2-Bromophenyl)thio]imidazo[1,5-a]quinoxaline

A mixture of 1F (40 mg; 0.2 mmol), o-bromothiophenol (26 μL; 0.2 mmol) and potassium carbonate (70 mg; 0.5 mmol) in 0.5 mL of DMF was stirred at room temperature for 18 hr. An additional amount of bromothiophenol (13 μl; 0.1 mmol) was added and the reaction was stirred 2 hr. The reaction mixture was partitioned between EtOAc, and water. The organic layer was washed with 1N NaOH, water, and brine. Drying (MgSO$_4$) and concentration afforded a solid residue. The residue was recrystallized from CH$_2$Cl$_2$/hexane and allowed to stand at 5° C. for 18 hr. Filtration and drying afforded 53 mg (75%) of the title product as a tan crystalline solid. [mp 191–192° C.; HPLC: Retention time=15.25 minutes, HPLC conditions as described in Example 1.]

EXAMPLE 7

Preparation of 4-(2-Chloro-6-methylphenoxy)-7,8-dimethoxyimidazo[1,5-a]quinoxaline

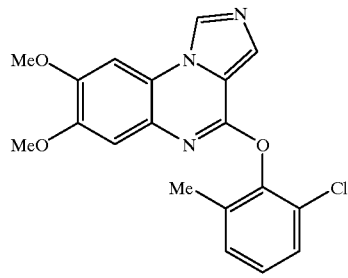

A mixture of 4-chloro-7,8-dimethoxyimidazo[1,5-a]quinoxaline, prepared as described in U.S. application Ser. No. 09/097,338, "Imidazoquinoxaline Protein Tyrosine Kinase Inhibitors," filed by Joel C. Barrish et al. concurrently herewith (20 mg, 0.076 mmol), potassium carbonate (52 mg, 0.38 mmol) and 2-chloro-6-methylphenol (13 mg, 0.091 mmol) in 0.5 mL of dry DMF was heated at 80° C. overnight. Upon cooling, the solvent was removed under reduced pressure and the residue was purified by preparative HPLC to give 9.0 mg of the title compound as a tan solid. HPLC Ret. time=4.075 min (HPLC Conditions: 0% B to 100% B; 4 minute gradient; 2 minute hold; 4 mL/min.; 254 nm; YMC S5 C18 Rapid Resolution column 4.6×50 mm; A: 90% H$_2$O –10% MeOH–0.2% H$_3$PO$_4$; B: 10% H$_2$O–90% MeOH–0.2% H$_3$PO$_4$).

What is claimed is:

1. An imidazoquinoxaline compound of the following formula I or a salt thereof:

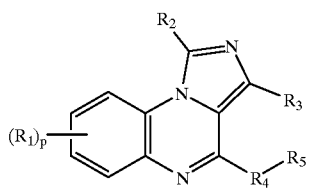

(I)

where
p is 0, 1, 2, 3 or 4;
each $R_1$, and $R_2$ are independently selected from:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more groups $Z_3$;
(2) —OH or —OR$_6$;
(3) —SH or —SR$_6$;
(4) —C(O)$_q$H, —C(O)$_q$R$_6$ or —O—C(O)$_q$R$_6$, where q is 1 or 2;
(5) —SO$_3$H or —S(O)$_q$R$_6$;
(6) halo;
(7) cyano;
(8) nitro;
(9) —Z$_4$—NR$_7$R$_6$;
(10) —Z$_4$—N(R$_9$)—Z$_5$—NR$_{10}$R$_{11}$;
(11) —Z$_4$—N(R$_{12}$)—Z$_5$—R$_6$;
(12) —SiR$_{13}$R$_{14}$R$_{15}$;
(13) —P(O)(OR$_6$)$_2$;
(14) —CH=N—OR$_6$;
(15) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
(16) any two groups $R_1$ may, together with the carbons to which they are attached, form a heterocyclo group, which group is unsubstituted or substituted with $Z_1$, $Z_2$ and $Z_3$;

$R_3$ is
(1) hydrogen or *$R_6$,
where *$R_6$ is alkyl, alkenyl, alkynyl, cycloalkyl, cycloalkylalkyl, cycloalkenyl, cycloalkenylalkyl, aryl, aralkyl, or heterocycoalkyl, each of which is unsubstituted or substituted with $Z_1$, $Z_2$ and one or more groups $Z_3$;
(2) —OH or —OR$_6$;
(3) —SH or —SR$_6$;
(4) —C(O)H, —C(O)R$_6$ or —O—C(O) R$_6$;
(5) —SO$_3$H or —S(O)$_q$R$_6$ where q is 1 or 2;
(6) halo;
(7) cyano;
(8) nitro;
(9) —Z$_4$—NR$_7$R$_8$;
(10) —Z$_4$—N(R$_9$)—Z$_5$—NR$_{10}$R$_{11}$;
(11) —Z$_4$—N(R$_{12}$)—Z$_5$—R$_6$;
(12) —SiR$_{13}$R$_{14}$R$_{15}$;
(13) —P(O)(OR$_6$)$_2$; or
(14) —CH=N—OR$_6$;

$R_4$ is oxygen, or sulfur;
$R_5$ is alkenyl, aryl, or aromatic heterocyclo, each of which is unsubstituted or substituted with $Z_1$, $Z_2$ and one or more groups $Z_3$;
$R_7$, $R_8$, $R_9$, $R_{10}$, $R_{11}$ and $R_{12}$;
(1) are each independently hydrogen or $R_6$;
(2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$, $R_{14}$ and $R_{15}$ are each independently:
(1) alkyl; or
(2) phenyl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i)

or (ii) which is substituted by one or more of the following groups (2) to (16) of the definition of $Z_1$, $Z_2$ and $Z_3$;
(2) —OH or —OZ$_6$;
(3) —SH or —SZ$_6$;
(4) —C(O)$_q$H, —C(O)$_q$Z$_5$ or —O—C(O)$_q$Z$_6$;
(5) —SO$_3$H or —S(O)$_q$Z$_6$;
(6) halo;
(7) cyano;
(8) nitro;
(9) —Z$_4$—NZ$_7$Z$_8$;
(10) —Z$_4$—N(Z$_9$)—Z$_5$—NZ$_7$Z$_8$;
(11) —Z$_4$—N(Z$_{10}$)—Z$_5$—Z$_6$;
(12) —Z$_4$—N(Z$_{10}$)—Z$_5$—H;
(13) oxo;
(14) —O—C(O)—Z$_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—(CH$_2$)$_q$—O—;

$Z_4$ and $Z_5$ are each independently:
(1) a single bond;
(2) —Z$_{11}$—S(O)$_q$—Z$_{12}$—;
(3) —Z$_{11}$—C(O)—Z$_{12}$—;
(4) —Z$_{11}$—C(S)—Z$_{12}$—;
(5) —Z$_{11}$—O—Z$_{12}$—;
(6) —Z$_{11}$—S—Z$_{12}$—;
(7) —Z$_{11}$—O—C(O)—Z$_{12}$—; or
(8) —Z$_{11}$—C(O)—O—Z$_{12}$—;

$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and $Z_{11}$ and $Z_{12}$ are each independently:
(1) a single bond;
(2) alkylene;
(3) alkenylene; or
(4) alkynylene;

wherein the term "heterocyclo" refers to fully saturated or unsaturated, including aromatic or nonaromatic cyclic groups, selected from 4 to 7 membered monocyclic, 7 to 11 membered bicyclic, or 10 to 15 membered tricyclic ring systems, which have at least one heteroatom in at least one carbon atom-containing ring where each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized and wherein the heterocyclic group may be attached at any available heteroatom or carbon atom of the ring or ring system.

2. A compound of claim 1, wherein p is 0, 1 or 2.

3. A compound of claim 1, wherein each $R_1$ is independently selected from hydrogen, alkyl, alkoxy, nitro, aryl, halo, heterocyclo, —Z$_4$—NR$_7$R$_8$ or —Z$_4$—N(R$_{12}$)—Z$_5$—R$_6$.

4. A compound of claim 1, wherein $R_2$ is hydrogen or alkyl.

5. A compound of claim 1, wherein $R_3$ is hydrogen or alkyl.

6. A compound of claim 1, wherein $R_5$ is optionally substituted aryl.

7. A compound of claim 1, wherein said compound is free of the corresponding 1,2-regioisomer.

8. A compound of claim 1, which compound of the formula I or salt thereof is selected from the group consisting of:
4-(2-Bromophenoxy)imidazo[1,5-a]quinoxaline;
4-[(2-Bromophenyl)thio]imidazo[1,5-a]quinoxaline; and
4-(2-Chloro-6-methylphenoxy)-7,8-dimethoxyimidazo[1,5-a]quinoxaline.

9. A pharmaceutical composition for the treatment of a protein tyrosine kinase-associated disorder, comprising a pharmaceutically acceptable vehicle or diluent and at least one compound of claim 1.

10. A pharmaceutical composition of claim 9, wherein said compound of the formula I or salt thereof is selected from the group consisting of:
4-(2-Bromophenoxy)imidazo[1,5-a]quinoxaline;
4-[(2-Bromophenyl)thio]imidazo[1,5-a]quinoxaline; and
4-(2-Chloro-6-methylphenoxy)-7,8-dimethoxyimidazo[1,5-a]quinoxaline.

11. An imidazoquinoxaline compound of the following formula I or a salt thereof:

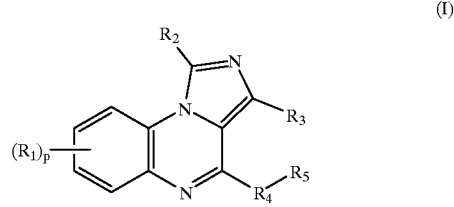

(I)

where
p is 0, 1, 2, 3 or 4;
each $R_1$, and $R_2$ are independently selected from:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more groups $Z_3$;
(2) —OH or —OR$_6$;
(3) —SH or —SR$_6$;
(4) —C(O)$_q$H, —C(O)$_q$R$_6$ or —O—C(O)$_q$R$_6$, where q is 1 or 2;
(5) —SO$_3$H or —S(O)$_q$R$_6$;
(6) halo;
(7) cyano;
(8) nitro;
(9) —Z$_4$—NR$_7$R$_8$;
(10) —Z$_4$—N(R$_9$)—Z$_5$—NR$_{10}$R$_{11}$;
(11) —Z$_4$—N(R$_{12}$)—Z$_5$—R$_6$;
(12) —SiR$_{13}$R$_{14}$R$_{15}$;
(13) —P(O)(OR$_6$)$_2$;
(14) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
(15) any two groups $R_1$ may, together with the carbons to which they are attached, form a heterocyclo group, which group is unsubstituted or substituted with $Z_1$, $Z_2$ and $Z_3$;

$R_3$ is
(1) hydrogen or $*R_6$,
where $*R_6$ is alkyl, alkenyl, alkynyl, cycloalkyl, cycloalkylalyl, cycloalkenyl, cycloalkenylalkyl, aryl, aralkyl, or heterocycloalkyl, each of which is unsubstituted or substituted with $Z_1$, $Z_2$ and one or more groups $Z_3$;
(2) —OH or —OR$_6$;
(3) —SH or —SR$_6$;
(4) —C(O)H, —C(O)R$_6$ or —O—C(O) R$_6$;
(5) —SO$_3$H or —S(O)$_q$R$_6$ where q is 1 or 2;
(6) halo;
(7) cyano;
(8) nitro;
(9) —Z$_4$—NR$_7$R$_8$;
(10) —Z$_4$—N(R$_9$)—Z$_5$—NR$_{10}$R$_{11}$;
(11) —Z$_4$—N(R$_{12}$)—Z$_5$—R$_6$;
(12) —SiR$_{13}$R$_{14}$R$_{15}$; or
(13) —P(O)(OR$_6$)$_2$;

$R_4$ is oxygen, sulfur, or a single bond;

$R_5$ is aryl, or heterocyclo, each of which is unsubstituted or substituted with $Z_1$, $Z_2$ and one or more groups $Z_3$;

$R_7$, $R_8$, $R_9$, $R_{10}$, $R_{11}$ and $R_{12}$:
(1) are each independently hydrogen or $R_6$;
(2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$, $R_{14}$ and $R_{15}$ are each independently:
(1) alkyl; or
(2) phenyl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —OZ$_6$;
(3) —SH or —SZ$_6$;
(4) —C(O)$_q$H, —C(O)$_q$Z$_6$ or —O—C(O)$_q$Z$_6$;
(5) —SO$_3$H or —S(O)$_q$Z$_6$;
(6) halo;
(7) cyano;
(8) nitro;
(9) —Z$_4$—NZ$_7$Z$_8$;
(10) —Z$_4$—N(Z$_9$)—Z$_5$—NZ$_7$Z$_8$;
(11) —Z$_4$—N(Z$_{10}$)—Z$_5$—Z$_6$;
(12) —Z$_4$—N(Z$_{10}$)—Z$_5$—H;
(13) oxo;
(14) —O—C(O)—Z$_6$;
(15) any two of $Z_1$, $Z_2$, and $Z_3$ may together be alkylene or alkenylene completing a 3- to 8membered saturated or unsaturated ring together with the atoms to which they are attached; or
(16) any two of $Z_1$, $Z_2$, and $Z_3$ may together be —O—(CH$_2$)$_q$—O—;

$Z_4$ and $Z_5$ are each independently:
(1) a single bond;
(2) —Z$_{11}$—S(O)$_q$—Z$_{12}$—;
(3) —Z$_{11}$—C(O)—Z$_{12}$—;
(4) —Z$_{11}$—C(S)—Z$_{12}$—;
(5) —Z$_{11}$—O—Z$_{12}$—;
(6) —Z$_{11}$—S—Z$_{12}$—;
(7) —Z$_{11}$—O—C(O)—Z$_{12}$—; or
(8) —Z$_{11}$—C(O)—O—Z$_{12}$—;

$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and $Z_{11}$, and $Z_{12}$ are each independently:
(1) a single bond;
(2) alkylene;
(3) alkenylene; or
(4) alkynylene;

wherein the term "heterocyclo" refers to fully saturated or unsaturated, including aromatic or nonaromatic cyclic groups, selected from 4 to 7 membered monocyclic, 7 to 11 membered bicyclic, or 10 to 15 membered tricyclic ring systems, which have at least one heteroatom in at least one carbon atom-containing ring where each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized and wherein the heterocyclic group may be attached at any available heteroatom or carbon atom of the ring or ring system.

12. A compound of claim 11, wherein p is 0, 1 or 2.

13. A compound of claim 11, wherein each $R_1$ is independently selected from hydrogen, alkyl, alkoxy, nitro, aryl, halo, heterocyclo, —Z$_4$—NR$_7$R$_8$ or —Z$_4$—N(R$_{12}$)—Z$_5$—R$_6$.

14. A compound of claim 11, wherein $R_2$ is hydrogen or alkyl.

15. A compound of claim 11, wherein $R_3$ is hydrogen or alkyl.

16. A compound of claim 11, wherein $R_5$ is optionally substituted aryl.

17. A pharmaceutical composition comprising a pharmacuetically acceptable vehicle and an effective amount of at least one compound of claim 11.

18. A compound of claim 11 selected from
4-Phenylimidazo[1,5-a]quinoxaline;
4-(4-Methoxyphenyl)imidazo[1,5-a]quinoxaline;
4-(4-Fluorophenyl)imidazo[1,5-a]quinoxaline; and
4-(2,6-Dimethylphenyl)imidazo[1,5-a]quinoxaline.

* * * * *